United States Patent
Bouckenooghe et al.

(10) Patent No.: US 10,507,231 B2
(45) Date of Patent: Dec. 17, 2019

(54) MATRIX IN BALL FORM AS A CELL CARRIER

(71) Applicant: Maco Pharma, Mouvaux (FR)

(72) Inventors: Thomas Bouckenooghe, Mons-en-Baroeul (FR); Pauline Bertholet, Halluin (FR); Bruno Delorme, Marcq en Baroeul (FR)

(73) Assignee: Maco Pharma, Mouvaux (FR)

( * ) Notice: Subject to any disclaimer, the term of this patent is extended or adjusted under 35 U.S.C. 154(b) by 106 days.

(21) Appl. No.: 15/548,418

(22) PCT Filed: Feb. 2, 2016

(86) PCT No.: PCT/EP2016/052137
§ 371 (c)(1),
(2) Date: Aug. 3, 2017

(87) PCT Pub. No.: WO2016/124569
PCT Pub. Date: Aug. 11, 2016

(65) Prior Publication Data
US 2018/0015147 A1  Jan. 18, 2018

(30) Foreign Application Priority Data

Feb. 3, 2015 (FR) ..................................... 15 00195

(51) Int. Cl.
| | |
|---|---|
| *A61K 38/36* | (2006.01) |
| *A61K 35/19* | (2015.01) |
| *A61L 27/22* | (2006.01) |
| *C12N 5/00* | (2006.01) |
| *C12M 1/12* | (2006.01) |
| *A61L 27/58* | (2006.01) |
| *A61L 27/56* | (2006.01) |
| *A61K 9/16* | (2006.01) |
| *A61K 35/12* | (2015.01) |
| *A61K 38/30* | (2006.01) |

(52) U.S. Cl.
CPC .......... *A61K 38/363* (2013.01); *A61K 9/1617* (2013.01); *A61K 35/12* (2013.01); *A61K 38/30* (2013.01); *A61L 27/225* (2013.01); *A61L 27/56* (2013.01); *A61L 27/58* (2013.01); *C12M 25/16* (2013.01); *C12N 5/0075* (2013.01); *C12N 2533/56* (2013.01); *C12N 2535/00* (2013.01); *C12N 2537/10* (2013.01)

(58) Field of Classification Search
None
See application file for complete search history.

(56) References Cited

U.S. PATENT DOCUMENTS

| | | | | |
|---|---|---|---|---|
| 2004/0247691 | A1* | 12/2004 | Marx | A61K 9/1658 424/491 |
| 2012/0156306 | A1* | 6/2012 | Weissman | A61K 38/18 424/532 |
| 2013/0273135 | A1* | 10/2013 | Brooks | A61L 27/34 424/426 |

FOREIGN PATENT DOCUMENTS

WO    9915637 A1    4/1999

OTHER PUBLICATIONS

Mariana B. Oliveira et al: "Injectable PEGylated fibrinogen cell-laden microparticles made with a continuous solvent- and oil-free preparation method" ACTA Biomaterialia vol. 13, Feb. 2015, pp. 78-87.
International Search Report of the ISA (EPO) dated Jul. 14, 2016.

* cited by examiner

*Primary Examiner* — Michelle F. Paguio Frising
(74) *Attorney, Agent, or Firm* — Patshegen IP LLC; Moshe Pinchas

(57) ABSTRACT

The invention relates to a matrix in ball form comprising cross-linked fibrinogen, the matrix being free from fibrin, as well as to a method for preparing such a matrix, comprising the following steps: (a) providing an initial composition comprising fibrinogen and a platelet factor; (b) injecting said initial composition into an oil heated to a temperature of 50° C. to 80° C. so as to form an emulsion; (c) mixing the emulsion thus obtained at a temperature of 50° C. to 80° C. until a matrix in ball form is obtained; and (d) isolating the matrix thus obtained. The matrix is used as a cell carrier.

17 Claims, 1 Drawing Sheet

MATRIX IN BALL FORM AS A CELL CARRIER

BACKGROUND OF THE INVENTION

The invention relates to a matrix in ball form, a method for preparing such a matrix and the use thereof as a cell carrier.

The invention applies to the field of cell culture, and in particular the expansion of cells used in the context of cell therapy, in bioproduction to produce bioactive molecules, or in research and development as cell models. Such cells are for example primary cells, pluripotent stem cells, stem cell lines or immortalized cell lines.

In particular, cell therapy, based on the use of adult stem cells, consists of replacing and regenerating the cells of unhealthy tissue by administering healthy and functional cells that have been selected, amplified and/or modified ex vivo.

The cell expansion step is necessary, since the different stem cell sources do not make it possible to obtain a sufficient quantity of cells for clinical use.

Currently, the adherent stem cells are cultivated in two-dimensional systems, in particular in plastic culture containers.

To obtain a larger quantity of cells, it is necessary to use a larger culture surface, for example by using a larger number of culture containers, increasing the size of the culture containers or using multilevel culture containers such as CellStack™ (Corning, USA). In these cases, however, the handling of the culture containers becomes more laborious.

Three-dimensional culture systems have also been tested, in particular using microcarriers in suspension.

For example, document US 2012/0009645 proposes a method for cultivating the pluripotent stem cells (embryonic stem cells, induced pluripotent stem cells) on microbeads, in the presence of a ROCK inhibitor. The microbeads are for example D53 cellulose beads or Cytodex 1 or 3 beads.

However, the use of such synthetic microcarriers has several drawbacks. First of all, these microcarriers have a low cell inoculation rate (less than 30%), causing a massive loss of cells of interest from the beginning of the expansion process. Next, the detachment of the cells from their carrier and the carrier-cell separation before injection into the patient remains a sizable problem. Lastly, when these synthetic microcarriers are used, they release plastic particles that cannot be blocked and that may therefore be injected into the patient at the same time as the cells of interest.

To offset the problem of cell adherence, it has been proposed to coat the microcarriers with molecules. However, these molecules are often expensive and/or of animal origin, which raises a biological safety issue.

For example, document US 2011/0111498 proposes a method for cultivating stem cells (mesenchymal stem cells, embryonic stem cells or induced pluripotent stem cells) on microcarriers in suspension. The microcarriers are for example synthetic beads (Toyopearl, Cytodex, DE52) having a positive charge and a coating of the Matrigel™, laminin or hyaluronic acid type capable of supporting cell growth.

Document WO 2009/134197 also describes a microcarrier, such as a Cytodex, for cell culture, coated with a plant protein hydrolysate, such as a soy peptone hydrolysate. This microcarrier has the advantage of not comprising animal proteins.

Document WO 2011/017050 proposes a microcarrier with no proteins of animal origin for cell culture having a polymer coating (e.g., swelling methacrylate) on which a polypeptide is grafted comprising the RGD sequence to promote attachment of the cells.

Cell microcarriers based on natural components also exist.

For example, document EP 1 015 570 proposes fibrin (ogen) microbeads as a cell carrier. These microbeads are prepared from fibrinogen, thrombin and factor XIII. However, the thrombin used as cross-linking agent is exogenous, which increases the preparation difficulty and the biological risk.

In the document by Eibes G., et al. (Maximizing the ex vivo expansion of human mesenchymal stem cells using a microcarrier-based stirred culture system. Journal of biotechnology, 2010, vol. 146, no. 4, pp. 194-197), it was shown that gelatin microporous beads (Cultispher S) are capable of adhering and causing mesenchymal stem cells to proliferate.

BRIEF SUMMARY OF THE INVENTION

The invention proposes a three-dimensional biocompatible matrix for cells making it possible to obtain an adhesion rate of more than 75%. This matrix is further easily degradable so as to be able to recover the cells. The matrix also has the advantage of being able to be prepared from a single biological product, without requiring proteins or other exogenous substances.

To that end and according to a first aspect, the invention relates to a matrix in ball form comprising cross-linked fibrinogen, said matrix being free from fibrin.

According to a second aspect, the invention relates to a method for preparing a matrix according to the first aspect, said method comprising the following steps:
(a) providing an initial composition comprising fibrinogen and a platelet factor,
(b) injecting said initial composition into an oil heated to a temperature of 50° C. to 80° C. so as to form an emulsion,
(c) mixing the emulsion thus obtained at a temperature of 50° C. to 80° C. until a matrix in ball form is obtained, and
(d) isolating the matrix thus obtained.

According to a third aspect, the invention relates to the use of a matrix according to the first aspect as a cell carrier.

Other aims and advantages will appear over the course of the following description.

DETAILED DESCRIPTION OF THE INVENTION

Figure 1:
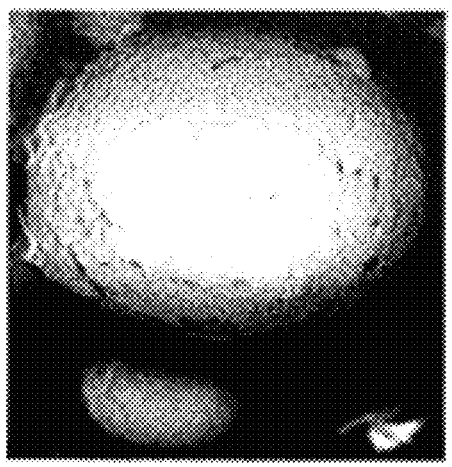
FIGS. 1 and 2 each show a photograph using scanning electron microscopy of a porous matrix according to the invention.

According to a first aspect, the invention relates to a matrix in ball form comprising cross-linked fibrinogen. The matrix is in particular free from fibrin.

"Matrix" refers to a solid or semi-solid three-dimensional structure on or in which cells can adhere and/or multiply.

The inventive matrix is in the form of a ball, i.e., it is spherical or spheroidal. It may have a regular or irregular shape.

The matrix is free from fibrin and comprises cross-linked fibrinogen, which makes it possible to obtain mechanically stable matrices not degraded during cell culture.

Fibrinogen is a soluble protein present in plasma. The fibrinogen protein is made up of three pairs of homologous peptide chains linked by disulfide bridges.

The cross-linked fibrinogen is fibrinogen in which at least two sites of the polypeptide chains are linked. The cross-linking is intramolecular, the linked sites then belong to the same fibrinogen and/or extramolecular molecule, two or more fibrinogen molecules are then linked. The cross-linked fibrinogen is insoluble in water and organic solvents.

In vivo, during plasma coagulation, the fibrinogen is cleaved by the action of the thrombin into fibrin monomers. The fibrin monomers will then polymerize into fibrin, which is unstable. The factor XIIIA will lastly allow the cross-linking of the fibrin polymer so as to stabilize it.

The cross-linking of the fibrinogen is consequently a non-natural process that was surprisingly obtained by the applicant from a specific initial composition. The cross-linked fibrinogen matrix of the invention is a synthetic fibrinogen matrix that in particular has a non-natural three-dimensional structure in ball form.

Advantageously, the fibrinogen contained in the matrix has not been physically and/or chemically functionalized, for example by pegylation. The fibrinogen contained in the initial composition is a natural fibrinogen that has not been modified by humans.

According to one particular embodiment, the initial composition comprises soluble fibrinogen. More particularly, the initial composition comprises plasma, which is a fibrinogen source. Still more particularly, the plasma is human plasma.

In particular, the fibrinogen is cross-linked by a platelet factor.

A platelet factor refers to one or several substances contained or secreted by the platelets. In particular, the platelet factor is a substance contained in a platelet lysate.

A platelet lysate refers to the product of lysis of the platelets, i.e., the product obtained after disintegration of the cell membrane that leads to the release of the molecules (growth factors, cytokines) normally contained inside platelets.

Lysis of the platelets is for example obtained by one or several freezing/thawing cycles, ultrasound or solvent/detergent treatment.

The cross-linking of the fibrinogen is made possible by the presence of the platelet factor. The preparation method described below carried out from an initial plasma composition without platelets in place of an initial platelet lysate composition did not result in matrix formation. Substance(s) of the platelet lysate leading to the cross-linking of the fibrinogen without fibrin formation are not known.

In particular, the cross-linking occurs without needing to add a chemical substance such as glutaraldehyde or a carbodiimide derivative or a xenogenic substance such as nonhuman thrombin, genipin or a sugar.

The matrix thus has the advantage of only containing proteins of human origin. The matrix is thus biocompatible, i.e., non-toxic with respect to cells, tissues and organs.

According to one embodiment, the matrix has a diameter comprised between 20 µm and 2 mm, in particular between 50 µm and 1000 µm. For example, the matrix has a diameter comprised between 200 and 800 µm.

In particular, the matrix according to the invention is a porous matrix, i.e., it has a plurality of interstices or orifices in its structure.

In particular, the matrix according to the invention has pores with a diameter smaller than 1 µm.

The inventive matrix being fibrinogen-based, it has the property of cell adhesion.

Due to the small size of the pores of the matrix, the cells that adhere thereto remain on its surface and do not migrate inside. This porous matrix is also capable of adsorbing small bioactive agents such as growth factors, cytokines, hormones or other active ingredients.

According to one particular embodiment, the matrix further comprises at least one bioactive agent such as a cell, a protein, for example a growth factor, a medicinal product, a hormone, a cytokine or a combination thereof.

The bioactive agent is encapsulated, absorbed, adsorbed and/or covalently bonded to the matrix.

In one particular example, the matrix comprises primary cells and/or cell lines. Examples of such cells are stem cells, fibroblasts, endothelial cells, chondrocytes, neuroblastoma cells, renal cells, liver cells, pancreatic cells, thyroid cells, glial cells, muscle cells, mouse mammary carcinoma cells and combinations thereof. Still more particularly, the cells are CHO (Chinese hamster ovary) cells, Vero cells or mesenchymal stem cells.

According to one specific embodiment, the cells are infected by a virus, a gene expressing a recombinant protein of interest or an exogenous DNA.

In particular, the matrix further comprises at least one growth factor such as IGF-1 (insulin-like growth factor-1). More particularly, the growth factor is endogenous, i.e., it is comprised in the initial composition comprising the fibrinogen intended to form the matrix.

The concentration of endogenous growth factor(s) in the matrix varies as a function of the preparation method and/or the initial concentration of growth factor(s) in the initial composition.

The matrices according to the invention have the advantage of being completely degradable by enzymatic and/or chemical action. This property facilitates the recovery of the cells after their expansion.

For example, enzymatic or non-enzymatic cell dissociation agents such as trypsin, the trypsin-EDTA combination, Accutase™ (Chemicon) or TrypLE™ (Gibco), are used to break down the matrices and thus detach the cells therefrom.

According to another aspect, the invention relates to a method for preparing a matrix according to the first aspect, comprising the following steps:

(a) providing an initial composition comprising fibrinogen and a platelet factor, (b) injecting said initial composition into an oil heated to a temperature comprised between 50 and 80° C. so as to form an emulsion, (c) mixing the emulsion thus obtained at a temperature comprised between 50 and 80° C. until a matrix in ball form is obtained, and (d) isolating the matrix thus obtained.

The starting product of the method is an initial composition comprising fibrinogen and a platelet factor. In particular, the initial composition comprises plasma as fibrinogen source and a platelet lysate as platelet factor source.

Advantageously, the plasma source and the platelet lysate source are shared. In this case, the initial composition is a platelet lysate obtained by lysis of platelets in suspension in plasma. For example, the initial composition is a platelet lysate obtained by lysis of one or several platelet concentrates or one or several platelet-rich plasmas.

According to one variant, the platelet concentrate comprises a platelet preservative additive solution. In this case, the quantity of plasma, and therefore of fibrinogen, in the platelet concentrate must remain sufficient to allow matrix formation.

In order to favor the spherical organization and reduce clumping of the matrices, the initial composition further comprises a surfactant agent.

"Surfactant agent" refers to an amphiphilic molecule, i.e., which has two parts with different polarities, one lipophilic (miscible in oil) and apolar, the other hydrophilic (miscible with water) and polar.

The surfactant agent serves to facilitate the formation of the emulsion, stabilize it and promote the dispersion of the formed droplets.

The surfactant agent is an anionic, cationic, amphoteric or non-ionic agent. Examples of surfactant agents are in particular sodium dodecyl sulfate, Triton X-100, Tween 20, Tween 80 and combinations thereof.

In particular, the composition comprises between 0.5 and 20% surfactant agent, in particular between 1 and 5%.

The method then comprises the injection of the initial composition into an oil heated to a temperature comprised between 50 and 80° C., so as to form an emulsion. Small droplets will then form and be dispersed in the hot oil.

According to one particular embodiment, the oil is an animal or plant oil, in particular a plant oil such as sunflower, olive or canola oil.

It is assumed that under the influence of the heat, inaccessible bonding sites of the fibrinogen proteins will be exposed and allow cross-linking, so as to make the fibrinogen insoluble in water and organic solvents.

If the initial composition is a platelet lysate obtained by lysis of the platelets in suspension in the plasma, the cross-linking of the fibrinogen is produced intrinsically, i.e., without using an outside substance.

The emulsion thus obtained is then mixed to form the matrix.

The manner of mixing the emulsion has an impact on the matrices. In particular, the mixing of the emulsion is performed by agitation at a speed comprised between 100 and 1500 cycles per minute, in particular greater than 700 cycles per minute. The higher the agitation speed is, the smaller the matrices will be.

The mixing is performed for a length of time comprised between 2 hours and 10 hours, in particular between 3 and 5 hours.

By varying the quantity and type of surfactant agent and/or by varying the agitation speed, it is possible to control the size of the matrices.

The step for isolating the formed matrices is performed by filtration, then successive washings of the matrices using an organic solvent in order to eliminate the traces of oil.

The method results in the formation of matrices of different sizes. In a variant, the method comprises, after isolating the matrices, the step of filtering the matrices through sieves with decreasing sizes in order to obtain calibrated matrices.

The method for obtaining the matrices according to the invention is a non-natural method that in particular requires contributing heat greater than 50° C.

The matrices obtained by this method from a platelet lysate are porous and essentially made up of cross-linked fibrinogen, and are free from fibrin.

According to a third aspect, the invention relates to the use of a matrix according to the first aspect as a cell carrier.

For cell culture, the matrices are placed in suspension in a culture medium contained in a culture container. The cells to be cultivated are then inoculated, i.e., placed in contact with the matrices.

For example, the matrices are used for cell expansion, production of proteins of interest and cell regeneration.

The matrices being biocompatible, they can be used in vivo with or without bioactive agent.

One particular advantage of the matrices according to the invention is their very high cell adhesion power. In fact, more than 75% of cells adhere to the matrices during the inoculation step.

Other applications for the matrices according to the invention are tissue regeneration, scar treatment, the controlled release of a medicinal product or stem cell selection.

Example

Ball Production 200 mL of sunflower oil is heated in a 500-mL container under magnetic agitation until it reaches 65° C. 50 mL of platelet lysate is then added into the hot oil. The solution thus obtained is kept under agitation at 65° C. until balls appear. The heating of the preparation is then stopped, and the agitation is maintained until it returns to ambient temperature. The preparation is then filtered on sieves with a calibrated size and the recovered balls are then washed three times using organic solvents (xylene, hexane and ethanol) and placed in a saline solution.

Due to their particular structure, the balls can also be kept in powdered form. The balls can then be kept at ambient temperature or at 4° C. for longer storage.

The balls thus obtained are spherical and have a diameter of 30 μm to 2000 μm. By screening, it is possible to obtain a population of balls having the desired size.

Figure 2:
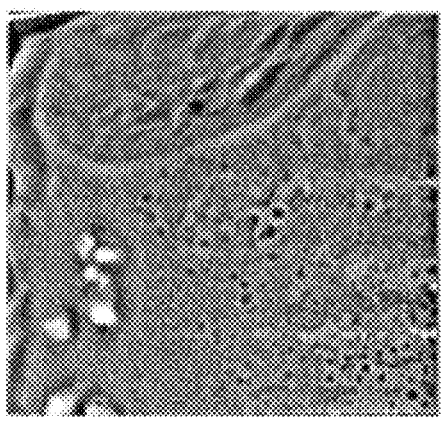

Scanning electron microscopy analyses made it possible to show a compact structure allowing cell adhesion (FIGS. 1 and 2).

Inoculation of the Balls by the Cells

Figure 3:
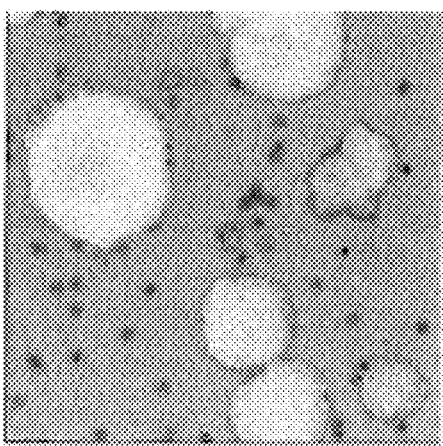
FIG. 3 shows a photograph with optical microscopy (×20) of matrices according to the invention in a culture medium and in the presence of cells.

The balls in solution were placed in contact with a known number of mesenchymal stem cells in a small volume of complete culture medium (10 mL). The cells adhere to the balls (FIG. 3).

After 4 hours of contact in an incubator at 37° C., the culture medium (without the balls) was collected and centrifuged. The number of cells not having adhered to the balls found in the supernatant was counted, making it possible to determine a cell adhesion rate of 75%.

Digestion of the Balls for Cell Recovery

The balls charged with the cells were kept in culture in order to obtain a sufficient number of cells. At the end of the cell culture period, the ball/cell complexes are recovered by centrifugation of the entire culture medium. The recovered pellet, made up of ball/cell complexes, is washed two times in PBS. After washing operations, an enzyme (TrypLE™) allowing total digestion of the balls without causing cell mortality is added on the pellet and placed at 37° C. for 20 minutes. After total digestion of the balls, the solution is centrifuged and the recovered cells can then be used.

Cell Proliferation Rate

Cell proliferation tests on balls according to the invention were performed, compared with polystyrene balls.

A murine cell line and human primary cells were inoculated at the same density on both types of balls. The quantity of cells not adhered was evaluated in order to precisely determine the quantity of adhered cells.

The cells on the balls were kept in culture for 10 days with the addition of fresh medium every 3 days. At the end of culture, the ball/cell complexes were recovered and the total quantity of generated cells was evaluated.

The tests allowed us to show, on the balls according to the invention, a cell amplification of 23 times for the murine cell line (versus 30 times for the polystyrene balls) and 14 times for the human primary line (versus 12 times for the polystyrene balls).

Characterization of the Balls

After the balls were produced, they were digested in order to study their composition precisely. Immunological assays made it possible to determine that the balls according to the invention were primarily made up of fibrinogen (on average present at 100 µg/mL). The assays made it possible to show the presence, within the balls according to the invention, of IGF-1 at a concentration of 0.3 pg/mL.

The presence of fibrin was not detected within the balls.

The invention claimed is:

1. A method for preparing a matrix comprising the following steps:
    (a) providing an initial composition comprising fibrinogen and a platelet factor the initial composition being free of exogenous thrombin;
    (b) injecting said initial composition in the absence of exogenous thrombin into an oil heated to a temperature of 50° C. to 80° C. so as to form an emulsion;
    (c) mixing the emulsion thus obtained at a temperature of 50° C. to 80° C. until a matrix in ball form is obtained; and
    (d) isolating the matrix thus obtained.

2. The method according to claim 1, wherein the initial composition is a platelet lysate obtained by lysis of platelets in suspension in plasma.

3. The method according to claim 2, wherein the platelet lysate is obtained from one or several platelet concentrates.

4. The method according to claim 1, wherein the initial composition further comprises a surfactant agent.

5. The method according to claim 4, wherein the composition comprises between 0.5 and 20% surfactant agent.

6. The method according to claim 1, wherein the mixing of the emulsion is done by agitation at a speed comprised between 100 and 1500 cycles per minute.

7. The method according to claim 1, wherein the oil is a plant oil.

8. The method according to claim 1, wherein the mixing of the emulsion is done for a length of time comprised between 2 hours and 10 hours.

9. A method for preparing a fibrin-free, cross-linked fibrinogen matrix, comprising the following steps:
    (a) providing is a platelet lysate free of exogenous thrombin and obtained by lysis of platelets in suspension in plasma;
    (b) injecting said platelet lysate into an oil heated to a temperature of 50° C. to 80° C. so as to form an emulsion;
    (c) mixing the emulsion thus obtained at a temperature of 50° C. to 80° C. until a matrix in ball form is obtained; and
    (d) isolating the matrix thus obtained.

10. A matrix in ball form prepared according to the method of claim 1, wherein the matrix is free from fibrin.

11. The matrix according to claim 10, wherein it is porous.

12. The matrix according to claim 11, wherein it has pores with a diameter smaller than 1 µm.

13. The matrix according to claim 10, wherein the fibrinogen is cross-linked via a platelet factor.

14. The matrix according to claim 10, wherein it has a diameter comprised between 20 µm and 2 mm, in particular between 50 µm and 1000 µm.

15. The matrix according to claim 10, wherein it further comprises at least one bioactive agent such as a cell, a protein, for example a growth factor, a medicinal product, a hormone, a cytokine or a combination thereof.

16. The matrix according to claim 15, wherein the protein is a growth factor such as IGF-1.

17. The matrix according to claim 10, on the surface of which cells are adhered.

* * * * *